US006034052A

United States Patent [19]

Körber et al.

[11] Patent Number: 6,034,052

[45] Date of Patent: Mar. 7, 2000

[54] MUSK FRAGRANCES

[76] Inventors: Alfred Körber, Steige 5; Peter Wörner, Schratweg 3, both of 37601 Holzminden; Horst Surburg, Meiernberg 9, 37603 Holzminden, all of Germany

[21] Appl. No.: 09/157,000

[22] Filed: Sep. 18, 1998

[30] Foreign Application Priority Data

Sep. 25, 1997 [DE] Germany .......................... 197 42 307

[51] Int. Cl.[7] .......................... A61K 7/46; C07C 69/66; C07C 69/34

[52] U.S. Cl. .......................... 512/26; 512/27; 512/28; 560/176; 560/190

[58] Field of Search .......................... 512/26, 27, 8; 560/176, 190

[56] References Cited

U.S. PATENT DOCUMENTS

| | | | |
|---|---|---|---|
| 4,105,672 | 8/1978 | Rueter et al. | 549/267 |
| 4,157,330 | 6/1979 | Rueter et al. | 549/267 |
| 4,165,321 | 8/1979 | Harris et al. | 549/228 |
| 4,218,379 | 8/1980 | Harris et al. | 549/267 |
| 4,331,603 | 5/1982 | Harris | 549/228 |
| 4,393,223 | 7/1983 | Harris | 549/266 |
| 4,499,288 | 2/1985 | Harris | 549/266 |
| 4,661,285 | 4/1987 | Harris et al. | 252/522 R |
| 4,709,058 | 11/1987 | Cahill, Jr. et al. | 549/267 |
| 5,717,111 | 2/1998 | Koehler et al. | 549/266 |

FOREIGN PATENT DOCUMENTS

| | | |
|---|---|---|
| 2547267 | 5/1977 | Germany . |

OTHER PUBLICATIONS

Steffen Arctander "Perfume & Flavor Chemicals (Aroma Chemicals)" Kekulé–Bibliothek, 1969.

*Primary Examiner*—Gabrielle Brouillette
*Assistant Examiner*—Monique T. Cole
*Attorney, Agent, or Firm*—Brinks Hofer Gilson & Lione

[57] ABSTRACT

Mixtures of ethylene dodecanedioate and ethylene undecanedioate which, because of their particular musk odor note, are products which can replace macrocyclic aromatic musk fragrances in inter alia perfume compositions.

9 Claims, No Drawings

MUSK FRAGRANCES

The present invention relates to mixtures of ethylene dodecanedioate and ethylene undecanedioate, to perfume oils comprising such mixtures as fragrance components and to products perfumed with such perfume oil.

BACKGROUND OF THE INVENTION

Compounds having a musk odor play a prominent role in the perfume industry. Because of their unique property of harmonizing perfume compositions, imparting character thereto and at the same time increasing tenacity, musk fragrances are nowadays to be found in significant amounts in almost every perfume oil. Accordingly, the worldwide annual requirement for musk fragrances is several thousand tons. By far the largest part is provided by "polycyclic aromatic" musk compounds. Typical examples of this class of compound are HHCB (commercial product, e.g. GALAXOLIDE®) and AHTN (commercial product, e.g. TONALIDE®)

HHCB

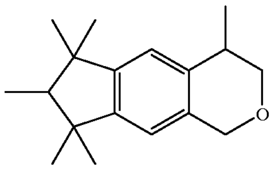

AHTN

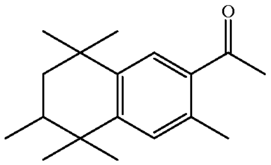

They are prepared in considerable amounts on an industrial scale and are thus available at a very favorable cost.

It has recently been discovered that polycyclic aromatic musk fragrances are not readily biodegradable and consequently, as extremely lipophilic compounds, exhibit bioaccumulative behaviour, i.e. they are able to accumulate in the fatty tissue of organisms.

In the perfume industry, there is thus an urgent need for biodegradable musk fragrances which are suitable both in terms of their odiferous properties as well as in terms of price level to replace the polycyclic aromatic compounds.

In contrast to the polycyclic aromatic compounds, macrocyclic musk fragrances are biodegradable. The market prices for these compounds, however, are several times those of polycyclic aromatic compounds. The general formula for macrocyclic musk fragrances is:

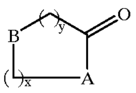

A = $CH_2$; O; O—$CH_2$—$CH_2$—O—CO;
B = $CH_2$; O; CH═CH;
x + y = 8 to 15.

One relatively good value compound within the group of macrocyclic musk fragrances is the cyclic ethylene glycol ester of dodecanedicarboxylic acid (ethylene dodecanedioate, available commercially, for example as AROVA N from Hüls). Because of its odiferous properties, however, this compound is not a suitable replacement for polycyclic aromatic musk fragrances. Surprisingly, we have, however, found that the addition of the lower homologue, the cyclic ethylene glycol ester of undecanedicarboxylic acid (ethylene undecanedioate), brings about an odiferous effect which is notable because the resulting mixture is considerably more like the odor type of the polycyclic and aromatic musk fragrances. Although the odiferous properties of ethylene undecanedioate have previously been described as "weakly musk-like, sweet" (S. Arctander; Perfume and Flavour Chemicals, published privately, Montclair N.J., 1969, Monograph 1228), there is no indication in the literature of an odiferous relation to polycyclic aromatic musk fragrances, making the observed effect in combination with ethylene dodecanedioate not foreseeable, but completely surprising.

SUMMARY OF THE INVENTION

The invention thus provides mixtures comprising a) ethylene dodecanedioate and b) ethylene undecanedioate, the amount of b) being from 5 to 60% by weight, preferably from 30 to 50% by weight, based on the total amount of (a+b).

As well as achieving the perfume character of polycyclic aromatic musk compounds, the use of such mixtures also significantly intensifies the mostly floral body note of perfume oils.

Mixtures with such compositions have the added advantage that they can be prepared at very favorable cost. Mixtures of dodecane- and undecanedicarboxylic acid are produced as low-cost by-products in the oxidation of cyclododecene to dodecanedicaboxylic acid (precursor for polyamide-1,12). This means that mixtures of ethylene dodecanedioate and ethylene undecanedioate are a low-cost alternative to polycyclic aromatic musk fragrances.

DESCRIPTION OF THE INVENTION

The mixtures of ethylene dodecanedioate and ethylene undecanedioate can be prepared in a manner known per se by esterification of the corresponding dicarboxylic acid mixture with ethylene glycol and subsequent thermal depolymerization of the resulting polyester mixture, e.g. analogously to the procedure given in German Patent 25 47 267. The polyester can be prepared by heating the dicarboxylic acid mixture with ethylene glycol, generally to from 130 to 200° C., preferably to from 150 to 170° C.

The depolymerization can be carried out thermally with heavy metal catalysis, generally between 200 and 300° C., preferably between 260 and 270° C. Preferred suitable catalysts are tin compounds, such as, for example, dibutyltin oxide, dibutyltin dilaurate and dibutyltin bis(2-ethylhexanoate). The reaction can be carried out without use of a solvent, but it is also possible to carry it out in the presence of a solvent.

The novel mixtures, because of their typical organoleptic properties, are especially suitable for use in perfume compositions and in this connection particularly as a replacement for polycyclic aromatic musk compounds. They can also be very readily combined with other fragrances in different varying mixing ratios to give new kinds of perfume compositions. In such perfume compositions, the amount of the novel mixtures is generally from 1 to 40% by weight, preferably from 5 to 20% by weight, based on the overall composition.

Perfume compositions of this type can be used not only in alcoholic solution as fine perfumes, but can also be used for perfuming cosmetics, for example creams, lotions, aerosols, toilet soaps etc., household products such as cleaners and laundry detergents, fabric softeners, disinfectants, textile treatment agents and other industrial products, the amount of perfume composition being from 0.1 to 40% by weight, preferably from 0.5 to 20% by weight, based on the perfumed product.

The percentages in the examples below are in each case by weight.

EXAMPLES

Example 1

Preparation of a mixture of ethylene dodecanedioate and ethylene undecanedioate:

105 g of ethylene glycol are added to 225 g of a technical-grade mixture of from 40 to 60% of dodecanedioic acid, from 30 to 50% of undecanedioic acid, from 3 to 8% of decanedioic acid and from 0 to 4% of nonanedioic acid, and the mixture is heated slowly to 150° C.; at about 130 to 140° C. the water starts to be eliminated. When all the water has been eliminated, the excess ethylene glycol is removed by increasing the temperature to 170° C. and evacuating the reaction apparatus slowly to a pressure of 1 mbar. 1.5 g of dibutyltin oxide is added to the dicarboxylic acid-ethylene glycol polyester which forms as residue, and the mixture, in the molten state, is slowly metered into a depolymerization apparatus which is preheated to 270° C. and fitted with a stirrer which passes close to the wall. At a pressure of 0.1 mbar, the monomeric cleavage products slowly distil off. Washing and activated carbon treatment produce a total of about 150 g of a mixture which has a pleasant, multi-faceted musk odour with a slightly floral-fatty basenote. According to analysis by gas chromatography, this mixture roughly corresponds to the composition of the starting material, i.e. comprises between 40 and 60% of ethylene dodecanedioate, from 30 to 50% of ethylene undecanedioate, from 3 to 8% of ethylene decanedioate and from 0 to 4% of ethylene nonanedioate.

Example 2

Preparation of a perfume oil using a mixture of ethylene dodecanedioate and ethylene undecanedioate A mixture comprising the following was prepared (all data in g):

| | |
|---|---|
| Styrolyl acetate | 2 |
| Dihydromyrcenol | 3 |
| Lemon oil | 15 |
| Aldehyde C14, so-called | 18 |
| Linalool | 20 |
| Phenyl ethyl alcohol | 10 |
| Citronellol | 10 |
| Benzyl acetate | 10 |
| Methyl dihydrojasmonate | 50 |
| Hexylcinnamaldehyde | 50 |
| Jasmin oil, synthetic | 20 |
| Ylang-Ylang oil, synthetic | 10 |
| Isomethylionone, gamma | 50 |
| Eugenol | 2 |
| Isoeugenol | 1 |
| Vanillin | 2 |
| Coumarin | 10 |
| H & R ORYCLON | 30 |
| Patchouli oil, colourless | 2 |
| H & R SANDEL | 50 |
| Bergamot oil, synthetic | 100 |
| Diethyl phthalate | 335 |
| Dipropylene glycol | 100 |

For the comparative test, 100 g of dipropylene glycol were in each case replaced by the same amount of the musk compounds a) GALAXOLIDE® 50% in diethyl phthalate, b) ethylene dodecanedioate, c) ethylene tridecanedioate (ethylene brassylate) and d) a mixture of ethylene dodecanedioate and ethylene undecanedioate, prepared as in Example 1. Scent evaluation produced the following results:

test mixtures a and d are the most similar in terms of odor, test mixture d has a more harmonious and voluminous odor than test mixtures b and c, the floral body note (bouquet) in test mixture d is exceedingly intensified compared to b and c, and test mixture d has a clearly complexer and richer fragrance compared to b and c.

What is claimed is:

1. A perfumed composition comprising:

ethylene dodecanedioate, ethylene undecanedioate, and a carrier, the perfumed composition having a musk note.

2. The composition of claim 1 wherein the amount of ethylene undecanedioate is from 5 to 60% by weight, based on the total weight of ethylene dodecanedioate and ethylene undecanedioate in the composition.

3. The composition of claim 1 wherein the amount of ethylene undecanedioate is from 30 to 50% by weight, based on the total weight of ethylene dodecanedioate and ethylene undecanedioate in the composition.

4. The perfumed composition of claim 1 wherein the total amount of ethylene dodecanedioate and ethylene undecanedioate comprises from 1 to 40% by weight of the perfume composition, based on the total weight of the perfumed composition.

5. The perfume composition of claim 1 wherein the total amount of ethylene dodecanedioate and ethylene undecanedioate comprises from 5 to 20% by weight of the perfumed composition, based on the total weight of the perfumed composition.

6. The perfumed composition of claim 1 wherein the carrier is selected from the group consisting of a fine perfume, cosmetic cream, cosmetic aerosol, toilet soap, cleaner, fabric softener, laundry detergent, disinfectant, and textile treatment agent.

7. The perfumed composition of claim 6 wherein the total amount of ethylene dodecanedioate and ethylene undecanedioate comprises from 0.1 to 40% by weight of the perfumed composition based on the total weight of the perfumed composition.

8. The perfumed composition of claim 6 wherein the total amount of ethylene dodecanedioate and ethylene undecanedioate comprises from 0.5 to 20% by weight of the perfumed composition based on the total weight of the perfumed composition.

9. The perfumed composition of claim 1 wherein the musk note is similar to that of a polycyclic aromatic musk fragrance.

* * * * *